United States Patent [19]

Comninellis et al.

[11] Patent Number: 4,880,571
[45] Date of Patent: Nov. 14, 1989

[54] PROCESS FOR THE PREPARATION OF 5-NITRO-1,4-NAPHTHOQUINONE

[75] Inventors: Christos Comninellis, Mex; Robert U. Osterwalder, Basel; Eric Plattner, Seltisberg; Gottfried Seifert, Magden, all of Switzerland

[73] Assignee: Ciba-Geigy Corporation, Ardsley, N.Y.

[21] Appl. No.: 921,918

[22] Filed: Oct. 22, 1986

[30] Foreign Application Priority Data

Oct. 24, 1985 [CH] Switzerland .......................... 4580/85

[51] Int. Cl.$^4$ ....................... C07C 50/12; C07L 50/00
[52] U.S. Cl. ................................................ 552/297
[58] Field of Search ..................................... 260/396 R

[56] References Cited

U.S. PATENT DOCUMENTS 3,873,580  3/1975  Rennie ........................... 260/396 R

FOREIGN PATENT DOCUMENTS 2436157  2/1975  Fed. Rep. of Germany ... 260/396 R
3222305  1/1983  Fed. Rep. of Germany ... 260/396 R

OTHER PUBLICATIONS

Chemical Abstracts vol. 55, 1547–8.
Ullmanns Encyklopädie der technischen Chemie 4. (4th Edition), neubearbeitete und erweiterte.
Auflage, Band 17 (vol. 17), milchsäure bis Petrolkoks (1979), pp. 121 & 392.
Chemical Abstracts (25 Benzenes) vol. 98, (1983), p. 521.
Chemical Abstract vol. 95(1981), pp. 671, 61677j.

Primary Examiner—Werren B. Lone
Attorney, Agent, or Firm—Kevin T. Mansfield; Edward McC. Roberts

[57] ABSTRACT

A process for the preparation of 5-nitro-1,4-naphthoquinones of formula

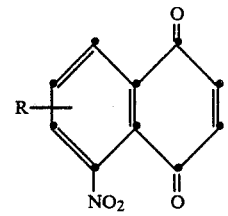

wherein R is hydrogen, a $C_1$-$C_4$alkyl radical or a $C_1$-$C_4$alkoxy radical, by oxidation of 1-nitronaphthalene or a suitably substituted 1-nitronaphthalene, which process comprises carrying out the reaction with manganese(III) sulfate as oxidizing agent or a mixture of manganese(III) sulfate and cerium sulfate.

The maganese(III) sulfate consumed can be regenerated electrolytically with good current yield. The process is environmentally safe, as the oxidizing agent and the solvent, if any, can be reused.

10 Claims, No Drawings

PROCESS FOR THE PREPARATION OF 5-NITRO-1,4-NAPHTHOQUINONE

The present invention relates to a process for the preparation of 5-nitro-1,4-naphthoquinones by oxidising corresponding 1-nitronaphthalenes with manganese(III) sulfate.

5-Nitro-1,4-naphthoquinone, referred to hereinafter for short as 5-nitronaphthoquinone, is an important dyestuff intermediate which is reacted with butadiene by a Diels-Alder reaction to 5-nitro1, 1,4,11,12-tetrahydroanthraquinone (q.v. for example N.N. Vorozhtsov et al., Zhur. Vsesoyuz. Khim. Obshchestva in D.I. Mendeleeva 5, 474 (1960) - Chem. Abstract, Vol. 55, 1547e), which is subsequently rearranged to give 1-hydroxyaminoanthraquinone or converted direct to 1-aminoanthraquinone, the starting material for numerous disperse and vat dyes (e.g. German Offenlegungsschrift 24 50 883).

Several processes for the preparation of 5-nitronaphthoquinone are described in the literature. In the two most important process variants, a start is made either from naphthalene, which is first nitrated in 1-position and then oxidised (Ullmann Vol. 17 (1979) p. 392), or direct from 1,4-naphtoquinone, which is nitrated in 5-position with nitrating acid (q.v. Ullmann, Vol. 17 (1979), p. 121). The process described herein relates to the first variant, viz. the oxidation using 1-nitronaphthalene or a substituted nitronaphthalene as starting material.

Economic and ecological considerations are increasingly focussing interest at the present time on the use of oxidising agents that can be easily recovered from the reaction mixture at the conclusion of the reaction and regenerated for reuse in a further oxidation reaction. Thus, for example, naphthoquinone is obtained by oxidation of naphthalene with cerium(IV) sulfate, using a melt of naphthalene and regenerating the cerium(III) sulfate formed during the reaction by electrolysis or ozonolysis (q.v. German Offenlegungsschrift 32 20 305). In a similar process, it is also possible to synthesise 5-nitronaphthoquinone from 1-nitronaphthalene (q.v. German Offenlegungsschrift 23 01 803), using ammonium persulfate as oxidising agent in combination with cerium(IV) sulfate and silver nitrate. The process is carried out in a two-phase system consisting of an aqueous phase and an organic phase and the persulfate consumed is regenerated by electrolysis.

In the search for further oxidising agents which can be readily regenerated electrochemically, it has been found that it is also possible to oxidise 1-nitronaphthalene with manganese(III) sulfate to 5-nitronaphthoquinone. This method is economic with respect to the oxidising agent, and the manganese(II) sulfate formed during the reaction can be readily reoxidised with good current yield to manganese(III) sulfate by electrolysis. A good space/time yield is also obtained with this oxidising agent, as the process can be carried out in fairly concentrated medium.

Accordingly, the present invention relates to a process for the preparation of 5-nitro-1,4-naphthoquinones of formula

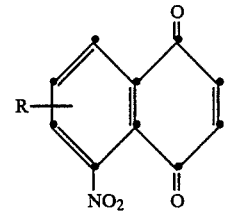

wherein R is hydrogen, a $C_1$–$C_4$ alkyl radical or a $C_1$–$C_4$ alkoxy radical, by oxidation of 1-nitronaphthalene or a suitably substituted 1-nitronaphthalene, which process comprises carrying out the reaction with manganese(III) sulfate as oxidising agent.

The starting 1-nitronaphthalenes are known or are obtainable by known methods. The process of this invention relates in particular to the preparation of unsubstituted 5-nitronaphthoquinone starting from 1-nitronaphthalene.

The 1-nitronaphthalene or substituted 1-nitronaphthalene is conveniently treated either direct in the melt with a solution or suspension of manganese(III) sulfate in sulfuric acid, or dissolved beforehand in a water-immiscible solvent or in a solvent of only limited miscibility with water, and this solution is then thoroughly mixed with the above solution or suspension of manganese(III) sulfate in sulfuric acid. Suitable solvents are, of course, only those that are inert under the reaction conditions, i.e. that are neither oxidised by the manganese(III) salt nor attacked by the sulfuric acid. It is preferred to use non-polar aprotic solvents, in particular aromatic or aliphatic hydrocarbons which are liquid at room temperature. Most preferably chlorobenzene, dichlorobenzene or nitrobenzene is employed as solvent. Other suitable solvents are chlorinated biphenyls, 1,2,4-trichlorobenzene or tetrachloroethylene. The solvents may be used individually as well as in admixture, for example technical mixtures of dichlorobenzenes. The aliphatic solvents are preferably unbranched and/or branched aliphatic hydrocarbons with boiling points in the temperature range from 130° to 220° C., and are suitably for example isoparaffin mixtures with boiling ranges from 155° to 175° C., 170° to 190° C. and 190° to 210° C.

It is convenient to use 0.5 to 5 parts, preferably 1 to 2 parts, of solvent per 1 part of nitronaphthalene. The nitronaphthalene does not have to be completely dissolved and may also be in the form of an emulsion or is dispersed in the solvent.

The manganese(III) sulfate is employed in the form of a solution or suspension in sulfuric acid. Normally a 30 to 50 % suspension of manganese(III) sulfate in sulfuric acid having a concentration of about 30 to 60 %, preferably 40 to 55 %, is used. As regards the ratio of nitronaphthalene to manganese(III) sulfate, it is convenient to use 1 to 6 moles, preferably 2 to 5 moles, of manganese(III) sulfate per 1 mole of nitronaphthalene. Amounts of less than 1 mole result in uneconomically low yields, whereas an amount of more than 6 moles of manganese(III) sulfate per mole of naphthalene impairs the selectivity of the reaction. The yield can be improved by adding cerium sulfate, with a catalytic amount being sufficient. It is advantageous to add the cerium sulfate [$Ce_2(SO_4)_3$] in a concentration of 0.1 to 10 mol%, preferably 1 to 5 mol%, based on the amount of manganese(III) sulfate.

The electrolytic reoxidation of the manganese(II) sulfate can be carried out in any type of electrolytic cell. Suitable cathodes are materials conventionally employed in electrochemical reactions, e.g. metals such as lead, metal alloys, activated metals, metal oxide electrodes, carbon electrodes, and "Glassy-Carbon®" electrodes. Suitable anodes are platinum, lead, "Glassy-Carbon®" and $PbO_2$ on titanium. As the chemical oxidation and the electrochemical reoxidation are carried out successively in separate steps, an electrolytic cell without diaphragms can be used. The electrolysis will normally be carried out at a voltage of 2 to 5 volts and a current density of about 400 mA per $cm^2$. The manganese(II) sulfate is reoxidised to manganese(III) sulfate in a conversion of more than 90 %.

The chemical oxidation of nitronaphthalene to nitronaphthoquinone is generally carried out in the temperature range from 40° to 90° C., preferably from 55° to 70° C., whereas the electrolysis is carried out in the temperature range from 50° to 100° C.

The 5-nitronaphthoquinones obtained by the process of this invention are isolated from the reaction mixture in conventional manner. If the process is carried out without a solvent, then the product, together with unreacted starting material, is extracted with an organic solvent from the reaction mixture containing sulfuric acid. Extraction is preferably effected with a benzene or benzene derivative such as chlorobenzene, nitrobenzene, xylene or, most preferably, toluene. It is expedient to use a solvent in which the starting nitronaphthalene is readily soluble even at low temperature and from which the nitronaphthoquinone precipitates upon cooling and can thus be isolated by simple cooling crystallisation. The precipitated product is isolated by filtration and dried, affording 5-nitronaphthoquinone or the corresponding alkyl or alkoxy derivatives in 90 to 95 % purity. The nitronaphthalene remaining in the solvent can be recovered and used as starting material for a further oxidation cycle. The inorganic phase is introduced into an electrolytic cell and the manganese(III) sulfate consumed is regenerated electrolytically.

Working up is extremely simple if the reaction is carried out in a two-phase system. When the reaction is complete, both phases are separated. Residues of product and starting material are extracted from the inorganic phase, preferably with the solvent employed in the reaction, and then passed into an electrolytic cell as described above. The organic phases are combined and the naphthoquinone is isolated therefrom by known methods, e.g. again by cooling crystallisation. Unreacted nitronaphthalene is used again as starting material. The solvent is also recovered and reused for the next batch.

Thus no environmentally harmful residues occur, irrespective of whether the process is carried out with or without a solvent. This is the great advantage of the process of the invention.

The invention is illustrated by the following Examples, in which parts and percentages are by weight.

EXAMPLE 1

173 parts of 1-nitronaphthalene are charged to a heatable reactor equipped with stirrer and a Pt/AgCl electrode and fused by heating to 60° C. To the melt are then added, over about 30 minutes, a mixture of 2200 parts of a c. 36 % suspension of manganese(III) sulfate in sulfuric acid, and 470 parts of water. The molar ratio of 1-nitronaphthalene to manganese(III) sulfate is 1:2. The manganese sulfate suspension additionally contains 0.9 mol% of cerium(III) sulfate, based on the amount of manganese(III) sulfate. The amount of water added is such that the concentration of the sulfuric acid at the conclusion of the reaction is 42 to 43 %. The reaction mixture is stirred at a temperature of 60° C. until the manganese(III) sulfate is consumed and has undergone complete conversion to manganese(II) sulfate. This can be easily determined by measuring the potential. 5-Nitro-1,4-naphthoquinone and unreacted 1-nitronaphthalene are then extracted from the reaction mixture with altogether 225 parts of toluene. The toluene phase containing the product is washed with altogether 1500 parts of water and then cooled to 0° to 5° C., whereupon 5-nitro-1,4-naphthoquinone crystallises out. The product is isolated by filtration, washed with 50 parts of toluene of 0° C. and then vacuum dried. The yield of 5-nitro-1,4-naphthoquinone is 50 to 60 % of theory, based on reacted 1-nitronaphthalene. The product has a purity of 90 to 95 %.

The mother liquid is taken to dryness at 70° C. under vacuum and the recovered 1-nitronaphthalene is reused for the next batch.

EXAMPLE 2

100 parts of 1-nitronaphthalene in 150 parts of chlorobenzene are charged to a double jacket reactor equipped with stirrer and heated to 70° C. Then 1526 parts of a suspension of manganese(III) sulfate in sulfuric acid are added. The concentration of the sulfuric acid is 45 % and the content of manganese(III) sulfate is c. 36 %. The manganese sulfate suspension additionally contains c. 5 mol% of cerium sulfate, based on the amount of manganese(III) sulfate. The manganese(III) sulfate is used in somewhat less than stoichiometric proportion, i.e. about 2.4 moles of $Mn_2(SO_4)_3$ per 1 mole of nitronaphthalene. The manganese(III) sulfate suspension is slowly added in portions over 1 to 2 hours. The reaction mixture is kept for 40 minutes at 70° C. and then stirring is discontinued. The phases are separated to give 238 parts of an organic phase containing 18 % of nitronaphthoquinone and 20 % of nitronaphthalene. The sulfuric acid phase is extracted with 50 parts of chlorobenzene, affording a further 50.5 parts of organic phase containing 4 % of nitronaphthoquinone and 4 % of nitronaphthalene. The total yield of 5-nitro-1,4-naphthoquinone is 38.3 parts, corresponding to a yield of 77 %, based on reacted nitronaphthalene. 49.6 parts of nitronaphthalene and 98 % of the chlorobenzene are recovered. The nitronaphthalene as well as the chlorobenzene are reused for the next batch.

EXAMPLE 3

A mixture of 70 parts of 1-nitronaphthalene and 100 parts of nitrobenzene are charged to a heatable double jacket reactor equipped with anchor stirrer, and heated to 60° C. Then 994 parts of a suspension of manganese(III) sulfate in sulfuric acid are added. The sulfuric acid concentration of the manganese sulfate suspension is 52.6 % and the content of manganese(III) sulfate is c. 35 %, corresponding to c. 2 moles of manganese(III) sulfate per 1 mole of 1-nitronaphthalene. The manganese sulfate suspension additionally contains c. 1 mol% of cerium sulfate, based on the amount of manganese(III) sulfate. The manganese(III) sulfate suspension is added in portions over 1½ to 2 hours. The batch is reacted for 105 minutes, then stirring is discontinued. Complete phase separation occurs after 15 minutes. The two phases are separated, to give 165 parts of an organic phase containing 20 % of nitronaphthoquinone and 22 % of nitronaphthalene. The organic phase is cooled to about 20° C. and the precipitated product is isolated by filtration and then dried at 70° C. Yield: 13 parts of product containing 85 % of 5-nitronaphthoquinone. Melting point: 138° to 140° C. Further product is isolated by extracting the inorganic phase with nitrobenzene. Total yield of 5-nitronaphtoquinone: 28.1 parts, corresponding to a yield of 73 %, based on reacted 1-nitronaphthalene.

EXAMPLE 4

Preparation of the suspension of manganese(III) sulfate in sulfuric acid by electrochemical oxidation of manganese(II) sulfate 8 parts of cerium(III) sulfate, 500 parts of manganese(II) sulfate monohydrate, 450 parts of water and 650 parts of 95 % sulfuric acid are mixed in a stirred reactor to give 1608 parts of electrolyte with a sulfuric acid concentration of 55.5 % and a manganese(II) content of 1.84 mol/kg of electrolyte. This electrolyte is charged to an electrolytic cell equipped with lead electrodes and the manganese(II) sulfate is oxidised to manganese(III) sulfate under the following conditions: temperature 85° C., current density 400 mA/cm$^2$, voltage 3.1–3.3 volts. After 3 hours electrolysis, corresponding to a current flow of 120 A.h, 95 % of the manganese(II) sulfate has been oxidised to manganese(III) sulfate, corresponding to a current yield of 69 %.

In the same manner, the manganese(II) sulfate formed at the conclusion of the chemical oxidation, in the course of which 1-nitronaphthalene is converted to 5-nitro-1,4-nitronaphthoquinone, is reoxidised to manganese(III) sulfate and can be reused for a subsequent batch as oxidising agent.

What is claimed is:

1. A process for the preparation of 5-nitro-1,4-naphthoquinones of formula

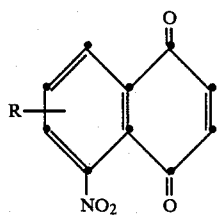

wherein R is hydrogen, a $C_1$–$C_4$ alkyl radical or a $C_1$–$C_4$ alkoxy radical, by oxidation of 1-nitronaphthalene or a suitably substituted 1-nitronaphthalene, which process comprises carrying out the reaction with manganese(III) sulfate as oxidizing agent.

2. A process according to claim 1, which comprises carrying out the reaction in a two-phase system consisting of a melt of nitronaphthalene and a solution or suspension of manganese(III) sulfate in sulfuric acid.

3. A process according to claim 1, which comprises using a solution of 1-nitronaphthalene in a non-polar aprotic solvent.

4. A process according to claim 3, which comprises using a solution of 1-nitronaphthalene in chlorobenzene, dichlorobenzene or nitrobenzene.

5. A process according to claim 1, wherein 1 to 6 moles of manganese(III) sulfate are used per 1 mole of nitronaphthalene.

6. A process for the preparation of 5-nitro-1,4-naphthoquinones of formula

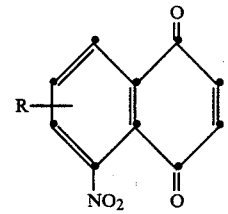

wherein R is hydrogen, a $C_1$–$C_4$ alkyl radical or a $C_1$–$C_4$ alkoxy radical, by oxidation of 1-nitronaphthalene or a suitably substituted 1-nitronaphthalene, which process comprises carrying out the reaction with a mixture of manganese(III) sulfate and cerium sulfate as oxidising agent.

7. A process according to claim 6, which comprises using 0.1 to 10 mol% of cerium sulfate, based on manganese(III) sulfate.

8. A process according to claim 7, which comprises using 1 to 5 mol% of cerium sulfate, based on manganese(III) sulfate.

9. A process according to claim 1, wherein manganese(II) sulfate formed during the reaction is reoxidised to manganese(III) sulfate by electrolysis and reused as oxidising agent.

10. A process according to claim 1, wherein 2 to 5 moles of manganese(III) sulfate are used per 1 mole of nitronaphthalene.

* * * * *